(12) United States Patent
Hektner (10) Patent No.: US 6,325,813 B1
(45) Date of Patent: *Dec. 4, 2001

(54) METHOD AND APPARATUS FOR STABILIZING VASCULAR WALL

(75) Inventor: Thomas R. Hektner, Medina, MN (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/135,875

(22) Filed: Aug. 18, 1998

(51) Int. Cl.[7] ................................................ A61M 29/00
(52) U.S. Cl. .................................... 606/191; 606/171
(58) Field of Search ................................ 606/191, 198, 606/195, 194, 185, 171; 604/95, 281-2; 623/1

(56) References Cited

U.S. PATENT DOCUMENTS

| Re. 35,352 | 10/1996 | Peters ........................................ 604/4 |
| Re. 35,459 | 2/1997 | Jonkman ................................ 604/164 |
| 3,667,069 | 6/1972 | Blackshear et al. ......................... 3/1 |
| 4,016,884 | 4/1977 | Kwan-Gett ............................ 128/348 |
| 4,165,747 | 8/1979 | Bermant ............................ 128/334 C |

(List continued on next page.)

FOREIGN PATENT DOCUMENTS

| 0 769 272 A1 | 10/1996 | (EP) . |
| 97-281410 | 7/1997 | (JP) . |
| 308752 | 9/1971 | (SU) . |
| 388738 | 11/1973 | (SU) . |
| 891076 | 12/1981 | (SU) . |
| 1822750 A1 | 6/1993 | (SU) . |
| 1600708 A1 | 10/1995 | (SU) . |
| WO 95/08364 | 3/1995 | (WO) . |
| WO 95/10218 | 4/1995 | (WO) . |
| WO 95/15192 | 6/1995 | (WO) . |
| WO 95/16476 | 6/1995 | (WO) . |
| WO 96/10375 | 4/1996 | (WO) . |
| WO 96/17644 | 6/1996 | (WO) . |
| WO 96/25886 | 8/1996 | (WO) . |
| WO 96/30072 | 10/1996 | (WO) . |
| WO 96/30073 | 10/1996 | (WO) . |
| WO 96/32882 | 10/1996 | (WO) . |
| WO 97/12555 | 4/1997 | (WO) . |
| WO 97/13463 | 4/1997 | (WO) . |
| WO 97/13468 | 4/1997 | (WO) . |
| WO 97/13471 | 4/1997 | (WO) . |
| WO 97/26939 | 7/1997 | (WO) . |
| WO 97/39784 | 10/1997 | (WO) . |
| WO 97/40751 | 11/1997 | (WO) . |

(List continued on next page.)

OTHER PUBLICATIONS

"The Current Status of Lasers in the Treatment of Cardiovascular Disease" by Jeffrey M. Isner and Richard H. Clarke, *IEEE*, vol. QE–20, No. 12, Dec. 1984, pp. 1406–1420.

"The Possibility of Myocardial Revascularization by Creation of a Left Ventriculocoronary Artery Fistula", by Ian Munro and Peter Allen, M.S., *Journal of Thoracic and Cardiovascular Surgery*, vol. 58, No. 1, Jul. 1969, pp. 25–32.

*Primary Examiner*—Kevin Truong
(74) *Attorney, Agent, or Firm*—Westman, Champlin & Kelly, P.A.

(57) ABSTRACT

A method and apparatus stabilize a vascular wall or vascular tissue during a surgical procedure. A stiffening member is inserted in a vessel to be accessed. The stiffening member is formed of a material having sufficient rigidity to significantly dampen movement of the vessel caused by normal heart action.

31 Claims, 10 Drawing Sheets

U.S. PATENT DOCUMENTS

| | | | |
|---|---|---|---|
| 4,173,981 | 11/1979 | Mortensen | 128/348 |
| 4,190,909 | 3/1980 | Ablaza | 3/1.4 |
| 4,230,096 | 10/1980 | Zeff et al. | 128/1 R |
| 4,546,499 | 10/1985 | Possis et al. | 623/1 |
| 4,562,597 | 1/1986 | Possis et al. | 623/1 |
| 4,566,453 | 1/1986 | Kumano et al. | 128/303.1 |
| 4,601,718 | 7/1986 | Possis et al. | 623/1 |
| 4,610,661 | 9/1986 | Possis et al. | 604/52 |
| 4,667,673 | 5/1987 | Li | 128/334 C |
| 4,690,684 | 9/1987 | McGreevy et al. | 623/12 |
| 4,710,192 | 12/1987 | Liotta et al. | 623/1 |
| 4,721,109 | 1/1988 | Healey | 128/334 R |
| 4,790,819 | 12/1988 | Li et al. | 604/59 |
| 4,803,984 | 2/1989 | Narayanan et al. | 128/334 R |
| 4,808,163 | 2/1989 | Laub | 604/105 |
| 4,819,640 | 4/1989 | Narayanan et al. | 128/334 R |
| 4,827,931 | 5/1989 | Longmore | 128/334 R |
| 4,869,263 * | 9/1989 | Segal et al. | 128/692 |
| 4,907,591 | 3/1990 | Vasconcellos et al. | 606/154 |
| 4,911,164 | 3/1990 | Roth | 606/148 |
| 4,995,857 | 2/1991 | Arnold | 600/16 |
| 5,011,469 | 4/1991 | Buckberg et al. | 604/4 |
| 5,037,428 | 8/1991 | Picha et al. | 606/155 |
| 5,047,039 | 9/1991 | Avant et al. | 606/148 |
| 5,053,041 | 10/1991 | Ansari et al. | 606/148 |
| 5,053,043 | 10/1991 | Gottesman et al. | 606/148 |
| 5,061,245 | 10/1991 | Waldvogel | 604/170 |
| 5,067,958 | 11/1991 | Sandhaus | 606/142 |
| 5,080,663 | 1/1992 | Mills et al. | 606/144 |
| 5,080,664 | 1/1992 | Jain | 606/148 |
| 5,104,402 | 4/1992 | Melbin | 623/1 |
| 5,144,961 | 9/1992 | Chen et al. | 128/898 |
| 5,201,706 * | 4/1993 | Noguchi et al. | 604/96 |
| 5,222,962 | 6/1993 | Burkhart | 606/148 |
| 5,222,963 | 6/1993 | Brinkerhoff et al. | 606/153 |
| 5,222,971 | 6/1993 | Willard et al. | 606/158 |
| 5,234,445 | 8/1993 | Walker et al. | 606/148 |
| 5,254,113 | 10/1993 | Wilk | 606/8 |
| 5,281,236 | 1/1994 | Bagnato et al. | 606/139 |
| 5,282,810 | 2/1994 | Allen et al. | 606/150 |
| 5,287,861 | 2/1994 | Wilk | 128/898 |
| 5,308,320 | 5/1994 | Safar et al. | 604/4 |
| 5,314,418 * | 5/1994 | Takano et al. | 604/282 |
| 5,314,436 | 5/1994 | Wilk | 606/153 |
| 5,314,472 | 5/1994 | Fontaine | 623/12 |
| 5,323,789 | 6/1994 | Berggren et al. | 128/898 |
| 5,330,486 | 7/1994 | Wilk | 606/139 |
| 5,330,496 * | 7/1994 | Alferness | 606/171 |
| 5,370,683 | 12/1994 | Fontaine | 623/1 |
| 5,382,257 | 1/1995 | Lewis et al. | 606/148 |
| 5,383,854 | 1/1995 | Safar et al. | 604/98 |
| 5,383,928 | 1/1995 | Scott et al. | 623/1 |
| 5,397,345 | 3/1995 | Lazarus | 623/1 |
| 5,403,333 | 4/1995 | Kaster et al. | 606/151 |
| 5,409,019 | 4/1995 | Wilk | 128/898 |
| 5,425,705 | 6/1995 | Evard et al. | 604/28 |
| 5,425,739 | 6/1995 | Jessen | 606/155 |
| 5,429,144 | 7/1995 | Wilk | 128/898 |
| 5,433,700 | 7/1995 | Peters | 604/4 |
| 5,437,684 | 8/1995 | Calabrese et al. | 606/153 |
| 5,441,507 | 8/1995 | Wilk | 606/139 |
| 5,443,497 | 8/1995 | Venbrux | 623/1 |
| 5,447,512 | 9/1995 | Wilson et al. | 606/139 |
| 5,449,372 | 9/1995 | Schmaltz et al. | 606/198 |
| 5,452,733 | 9/1995 | Sterman et al. | 128/898 |
| 5,456,714 | 10/1995 | Owen | 623/1 |
| 5,472,404 | 12/1995 | Volgushev | 600/36 |
| 5,476,453 * | 12/1995 | Mehta | 604/281 |
| 5,501,698 | 3/1996 | Roth et al. | 606/205 |
| 5,522,884 | 6/1996 | Wright | 623/2 |
| 5,527,319 | 6/1996 | Green et al. | 606/143 |
| 5,527,324 | 6/1996 | Krantz et al. | 606/155 |
| 5,536,251 | 7/1996 | Evard et al. | 604/93 |
| 5,540,677 | 7/1996 | Sinofsky | 606/8 |
| 5,540,701 | 7/1996 | Sharkey et al. | 606/153 |
| 5,545,171 | 8/1996 | Sharkey et al. | 606/148 |
| 5,554,162 | 9/1996 | DeLange | 606/153 |
| 5,556,414 | 9/1996 | Turi | 606/198 |
| 5,556,428 | 9/1996 | Shah | 623/13 |
| 5,562,728 | 10/1996 | Lazarus et al. | 623/1 |
| 5,569,272 | 10/1996 | Reed et al. | 606/151 |
| 5,569,274 | 10/1996 | Rapacki et al. | 606/158 |
| 5,571,090 | 11/1996 | Sherts | 606/144 |
| 5,571,215 | 11/1996 | Sterman et al. | 623/66 |
| 5,588,949 | 12/1996 | Taylor et al. | 600/166 |
| 5,591,179 | 1/1997 | Edelstein | 606/144 |
| 5,591,212 | 1/1997 | Keimel | 607/5 |
| 5,593,424 | 1/1997 | Northrup, III | 606/232 |
| 5,601,576 | 2/1997 | Garrison | 606/148 |
| 5,601,581 | 2/1997 | Fogarty et al. | 606/159 |
| 5,609,598 | 3/1997 | Laufer et al. | 606/142 |
| 5,613,937 | 3/1997 | Garrison et al. | 600/201 |
| 5,618,270 | 4/1997 | Orejola | 604/164 |
| 5,636,634 * | 6/1997 | Kordis et al. | 606/129 |
| 5,643,292 | 7/1997 | Hart | 606/144 |
| 5,653,744 | 8/1997 | Khouri | 623/1 |
| 5,655,548 | 8/1997 | Nelson et al. | 128/898 |
| 5,662,124 | 9/1997 | Wilk | 128/898 |
| 5,662,711 | 9/1997 | Douglas | 623/12 |
| 5,676,670 | 10/1997 | Kim | 606/108 |
| 5,682,906 | 11/1997 | Sterman et al. | 128/898 |
| 5,685,857 | 11/1997 | Negus et al. | 604/170 |
| 5,693,083 | 12/1997 | Baker et al. | 623/1 |
| 5,702,368 | 12/1997 | Stevens et al. | 604/171 |
| 5,702,412 | 12/1997 | Popov et al. | 606/159 |
| 5,715,832 | 2/1998 | Koblish et al. | 128/754 |
| 5,716,367 | 2/1998 | Koike et al. | 606/144 |
| 5,718,725 | 2/1998 | Sterman et al. | 623/2 |
| 5,722,426 | 3/1998 | Kolff | 128/898 |
| 5,725,521 * | 3/1998 | Mueller | 606/15 |
| 5,725,537 | 3/1998 | Green et al. | 606/143 |
| 5,727,569 | 3/1998 | Benetti et al. | 128/898 |
| 5,728,151 | 3/1998 | Garrison et al. | 623/2 |
| 5,735,290 | 4/1998 | Sterman et al. | 128/898 |
| 5,738,649 | 4/1998 | Macoviak | 604/43 |
| 5,738,652 | 4/1998 | Boyd et al. | 604/96 |
| 5,749,892 | 5/1998 | Vierra et al. | 600/204 |
| 5,752,526 | 5/1998 | Cosgrove | 128/898 |
| 5,755,682 | 5/1998 | Knudson et al. | 604/8 |
| 5,755,687 | 5/1998 | Donlon | 604/53 |
| 5,755,778 | 5/1998 | Kleshinski | 623/1 |
| 5,758,663 | 6/1998 | Wilk et al. | 128/898 |
| 5,766,151 | 6/1998 | Valley et al. | 604/96 |
| 5,769,812 | 6/1998 | Stevens et al. | 604/4 |
| 5,792,094 | 8/1998 | Stevens et al. | 604/4 |
| 5,795,325 | 8/1998 | Valley et al. | 604/53 |
| 5,797,920 | 8/1998 | Kim | 606/108 |
| 5,797,933 | 8/1998 | Snow et al. | 606/151 |
| 5,799,661 | 9/1998 | Boyd et al. | 128/898 |
| 5,800,450 | 9/1998 | Lary et al. | 606/180 |
| 5,800,522 | 9/1998 | Campbell et al. | 623/1 |
| 5,807,243 | 9/1998 | Vierra et al. | 600/204 |
| 5,807,318 | 9/1998 | St. Goar et al. | 604/53 |
| 5,810,757 | 9/1998 | Sweezer, Jr. et al. | 604/4 |
| 5,810,811 | 9/1998 | Yates et al. | 606/50 |
| 5,810,851 | 9/1998 | Yoon | 606/148 |
| 5,814,016 | 9/1998 | Valley et al. | 604/96 |
| 5,817,113 | 10/1998 | Gifford, III et al. | 606/153 |
| 5,823,956 | 10/1998 | Roth et al. | 600/374 |
| 5,824,070 | 10/1998 | Jarvik | 623/3 |
| 5,824,071 | 10/1998 | Nelson et al. | 623/3 |

| | | | | | |
|---|---|---|---|---|---|
| 5,827,265 | 10/1998 | Glinsky et al. .......................... 606/8 | WO 98/19607 | 5/1998 | (WO). |
| 5,829,447 | 11/1998 | Stevens et al. ...................... 128/898 | WO 98/19634 | 5/1998 | (WO). |
| 5,830,222 | 11/1998 | Makower ............................. 606/159 | WO 98/19636 | 5/1998 | (WO). |
| 5,830,224 | 11/1998 | Cohn et al. .......................... 606/167 | WO 98/31302 | 7/1998 | (WO). |
| | | | WO 98/32380 | 7/1998 | (WO). |
| | | | WO 98/35626 | 8/1998 | (WO). |

FOREIGN PATENT DOCUMENTS

| | | | | | |
|---|---|---|---|---|---|
| WO 98/06356 | 2/1998 | (WO). | WO 98/37814 | 9/1998 | (WO). |
| WO 98/07399 | 2/1998 | (WO). | WO 98/38939 | 9/1998 | (WO). |
| WO 98/10714 | 3/1998 | (WO). | WO 98/38941 | 9/1998 | (WO). |
| WO 98/15237 | 4/1998 | (WO). | WO 98/38942 | 9/1998 | (WO). |
| WO 98/16161 | 4/1998 | (WO). | WO 98/46119 | 10/1998 | (WO). |
| WO 98/16174 | 4/1998 | (WO). | WO 98/46158 | 10/1998 | (WO). |
| WO 98/17182 | 4/1998 | (WO). | | | |

* cited by examiner

Fig. 9C

METHOD AND APPARATUS FOR STABILIZING VASCULAR WALL

REFERENCE TO CO-PENDING APPLICATION

The following U.S. patent applications are hereby fully incorporated:

U.S. patent application Ser. No. 08/878,804, entitled PERCUTANEOUS CHAMBER-TO-ARTERY BYPASS, filed on Jun. 19, 1997, and assigned to the same assignee as the present application;

U.S. patent application Ser. No. 09/088,496, entitled PERCUTANEOUS CORONARY ARTERY BYPASS THROUGH A VENOUS VESSEL, filed on Jun. 1, 1998, and assigned to the same assignee as the present application;

U.S. patent application Ser. No. 08/813,038, entitled SYSTEM AND METHOD FOR PERCUTANEOUS CORONARY ARTERY BYPASS, filed on Mar. 6, 1997 and assigned to the same assignee as the present application;

U.S. patent application Ser. No. 08/813,040, entitled PERCUTANEOUS BYPASS WITH BRANCHING VESSEL, filed on Mar. 6, 1997 and assigned to the same assignee as the present application;

U.S. patent application Ser. No. 08/878,933, entitled PERCUTANEOUS ARTERY TO ARTERY BYPASS USING HEART TISSUE AS A PORTION OF A BYPASS CONDUIT, filed Jun. 19, 1997 and assigned to the same assignee as the present application; and U.S. patent application Ser. No. 08/812,878, entitled PERCUTANEOUS BYPASS BY TUNNELING THROUGH VESSEL WALL, filed on Mar. 6, 1997 and assigned to the same assignee as the present application.

BACKGROUND OF THE INVENTION

The present invention deals with stabilizing vascular surgical procedures. More specifically, the present invention deals with systems for stabilizing a vascular wall. During such procedures, such as during bypass procedures.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenosis include balloon angioplasty and pharmacological treatment. However, where the occlusion is quite hard, it can be quite difficult, if not impossible, to cross the occlusion with an angioplasty device. In addition, some coronary stenosis are too diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Also, the internal mammary artery (IMA) has also been used as a vein graft in performing a bypass. However, the IMA is typically best suited for use as a left anterior descending (LAD) graft and is commonly saved for that purpose. Further, open heart surgery requires quite a lengthy recovery period which involves an increased hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

SUMMARY OF THE INVENTION

A method and apparatus stabilize a vascular wall or vascular tissue during a surgical procedure. A stiffening member is inserted in a vessel to be accessed. A stiffening member is formed of a material having sufficient rigidity to significantly dampen movement of the vessel caused by normal heart action. In one embodiment, in which the vessel is a coronary artery, a stiffening member is inserted in the coronary artery, and a second stiffening member is inserted in a heart chamber proximate the coronary artery. The two stiffening members are deployed to dampen movement of the heart and vessel walls.

DETAILED DESCRIPTION OF THE PREFERRED EMBODIMENTS

Figure 1:
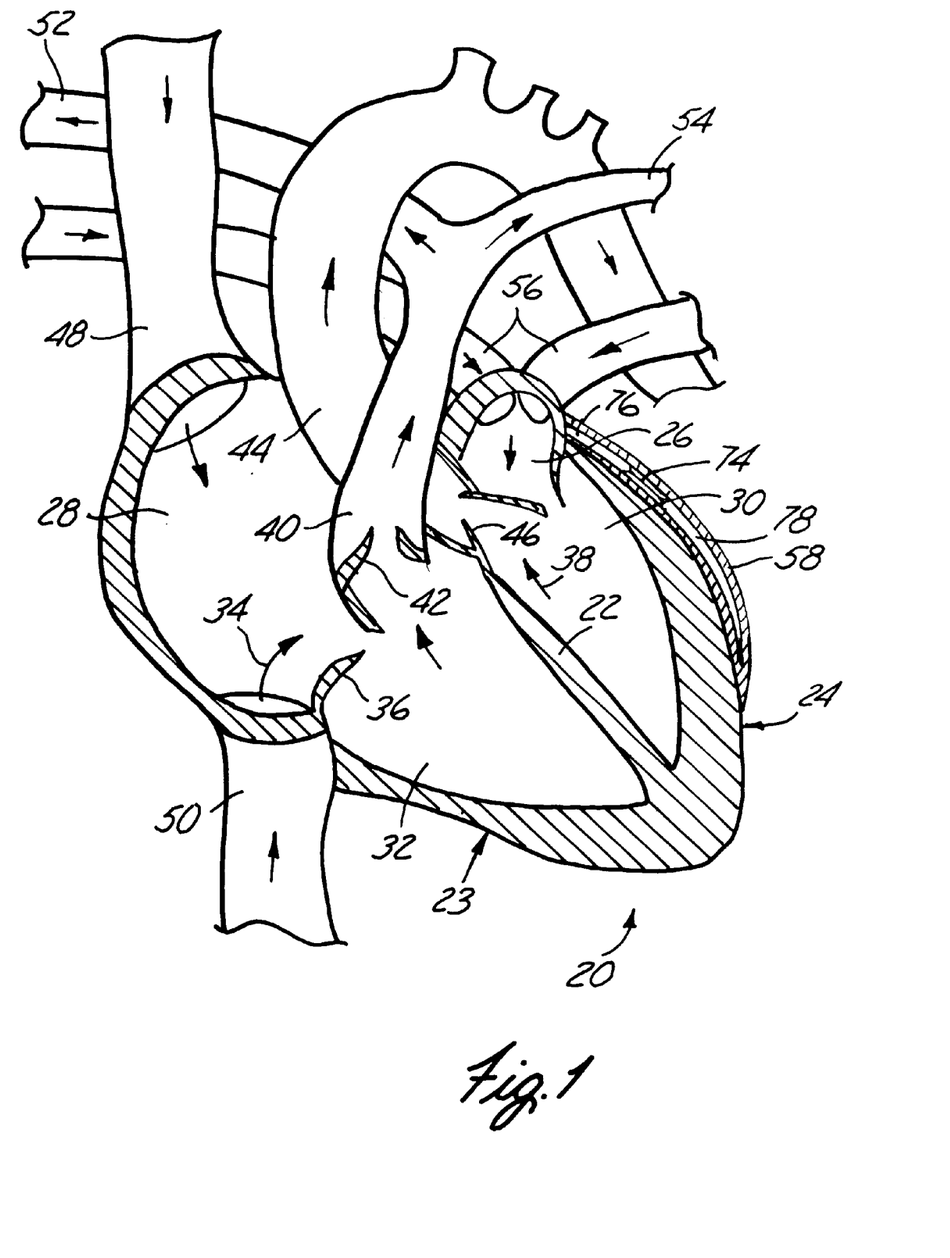
FIG. 1 illustrates a partial sectional view of a human heart and its associated proximate vascular system with a coronary artery having a restriction.

FIG. 1 illustrates a partially sectioned view of a human heart 20, and its associated vasculature. The heart 20 is subdivided by muscular septum 22 into two lateral halves, which are named respectively right 23 and left 24. A transverse constriction subdivides each half of the heart into two cavities, or chambers. The upper chambers consist of the left and right atria 26, 28 which collect blood. The lower chambers consist of the left and right ventricles 30, 32 which pump blood. The arrows 34 indicate the direction of blood flow through the heart. The chambers are defined by the epicardial wall of the heart.

The right atrium 28 communicates with the right ventricle 32 by the tricuspid valve 36. The left atrium 26 communicates with the left ventricle 30 by the mitral valve 38. The right ventricle 32 empties into the pulmonary artery 40 by way of the pulmonary valve 42. The left ventricle 30 empties into the aorta 44 by way of the aortic valve 46.

The circulation of the heart 20 consists of two components. First is the functional circulation of the heart 20, i.e., the blood flow through the heart 20 from which blood is pumped to the lungs and the body in general. Second is the coronary circulation, i.e., the blood supply to the structures and muscles of the heart 20 itself.

The functional circulation of the heart 20 pumps blood to the body in general, i.e., the systematic circulation, and to the lungs for oxygenation, i.e., the pulmonic and pulmonary circulation. The left side of the heart 24 supplies the systemic circulation. The right side 23 of the heart supplies the lungs with blood for oxygenation. Deoxygenated blood from the systematic circulation is returned to the heart 20 and is supplied to the right atrium 28 by the superior and inferior venae cavae 48, 50. The heart 20 pumps the deoxygenated blood into the lungs for oxygenation by way of the main pulmonary artery 40. The main pulmonary artery 40 separates into the right and left pulmonary arteries, 52, 54 which circulate to the right and left lungs, respectively. Oxygenated blood returns to the heart 20 at the left atrium 26 via four pulmonary veins 56 (of which two are shown). The blood then flows to the left ventricle 30 where it is pumped into the aorta 44, which supplies the body with oxygenated blood.

The functional circulation, however, does not supply blood to the heart muscle or structures. Therefore, functional circulation does not supply oxygen or nutrients to the heart 20 itself. The actual blood supply to the heart structure, i.e., the oxygen and nutrient supply, is provided by the coronary circulation of the heart, consisting of coronary arteries, indicated generally at 58, and cardiac veins. Coronary artery 58 resides closely proximate the endocardial wall of heart 24 and can have a restriction 74 or other disease to be treated. The coronary artery 58 includes a proximal arterial bed 76 between the aorta 44 and the restriction 74. Also, the coronary artery 58 includes a distal arterial bed 78 downstream from the restriction 74.

In order to treat vascular disease which includes a restriction (such as restriction 74 in coronary artery 58) one common technique is to bypass the restriction. In bypassing the restriction, the surgeon typically connects a conduit from a source to a destination. The source is typically some portion of the vasculature upstream of the restriction, while the destination is typically a portion of the stenosed artery, downstream of the restriction. The conduit can be any biologically compatible conduit, such as a saphenous vein graft, or an artificial, biologically compatible, material. Similarly, the source can be any number of suitable sources, such as those described in the above-referenced co-pending patent applications. The bypass can be performed by coupling a conduit to a branching vessel and the destination, tunneling through a vessel wall to the destination, forming a connection directly between a heart chamber and the destination, using a veinous vessel to branch around the restriction, or using other similar techniques.

During such bypass procedures, if the heart is kept beating, the area in the vasculature forming the source and destination are typically moving under the influence of normal heart action. Thus, the present invention is directed to a system by which the vascular tissue can be stabilized during such procedures. The present invention proceeds with respect to bypassing restriction 74 in coronary artery 58. However, it will be appreciated that the present invention can be used in substantially any vascular region which benefits from stabilization.

Figure 2A:
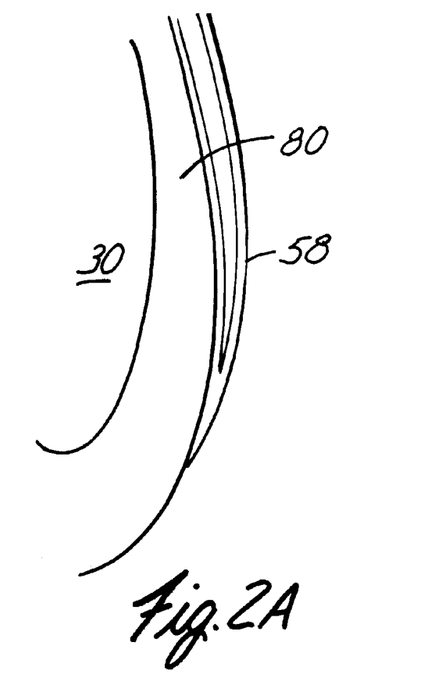
FIGS. 2A–2C illustrate movement of a coronary artery under the influence of normal heart action.
Figure 2B:
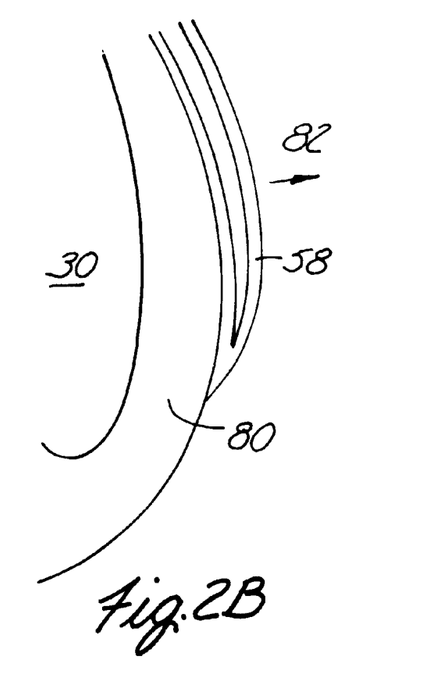
Figure 2C:
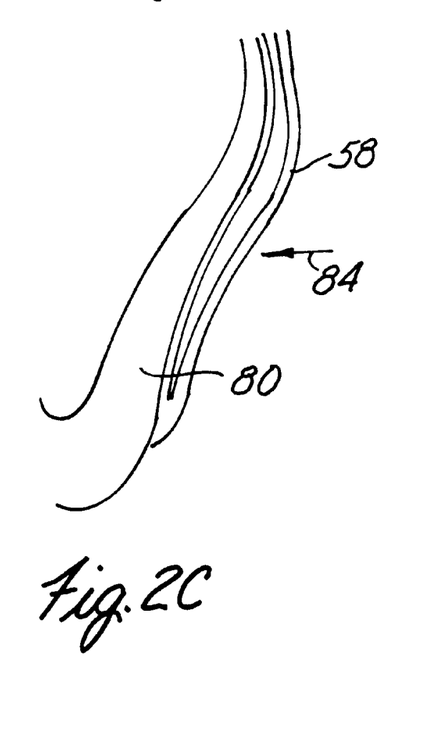

FIGS. 2A–2C illustrate the motion and movement of coronary artery 58 under the influence of heart action. FIG. 2A illustrates a portion of wall 80 of heart 24 over which coronary artery 58 resides. FIG. 2A also illustrates chamber 30 in heart 24 which corresponds to the left ventricle of heart 24. In FIG. 2A, coronary artery 58 is shown in a neutral position.

FIG. 2B illustrates the position 86 of coronary artery 58 during diastole, in which chamber 30 is filled with blood just prior to pumping the blood through aorta 44. FIG. 2B illustrates that, in this position, coronary artery 58 is moved generally outwardly relative to a central region of heart 24, in the direction indicated by arrow 82.

FIG. 2C illustrates the position 88 of coronary artery 58 during systole, when left ventricle 30 has pumped the blood out of left ventricle 30 into aorta 44. FIG. 2C illustrates that coronary artery 58 moves inwardly generally toward a central region of heart 24, in the direction indicated by arrow 84. The motion of the ventricular wall is more complex than a simple inward and outward movement. The figures illustrated only one form of heart movement for purposes of simplified explanation.

Figure 3:
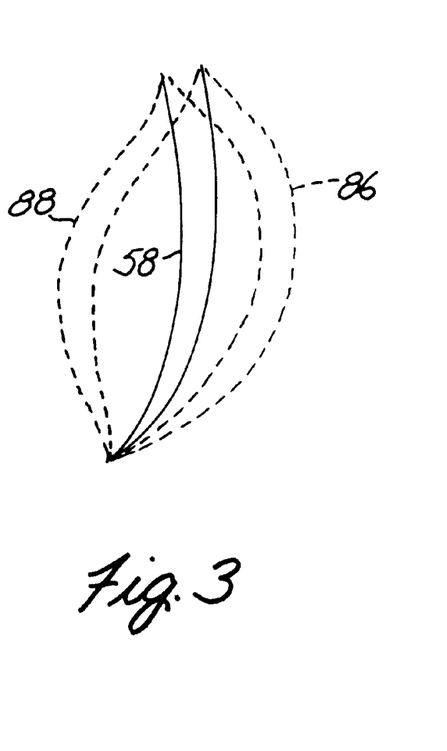
FIG. 3 is an exaggerated illustration of the movement of the coronary artery.

FIG. 3 illustrates coronary artery 58, shown in isolation. FIG. 3 better illustrates coronary artery 58 in position 86 shown in FIG. 2B (during diastole) and in the position 88 shown in FIG. 2C (during systole). FIG. 3 also illustrates coronary artery 58 in the neutral position. The displaced positions are illustrated in phantom in FIG. 3. Of course, the distances in FIG. 3 are enlarged, and the movement is exaggerated for the purposes of clarity.

Figure 4A:
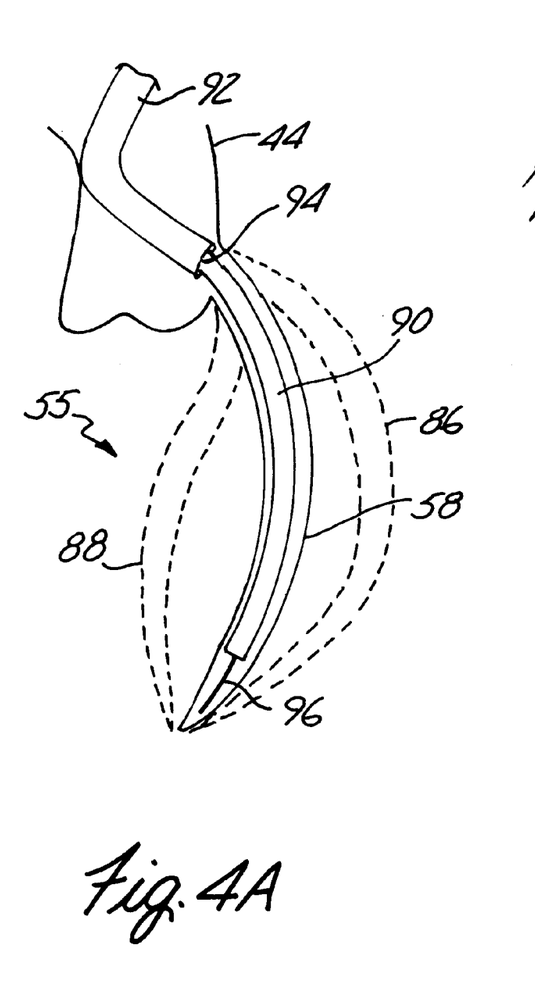
FIGS. 4A–4I illustrates placement of a stiffening member in the coronary artery in accordance with one aspect of the present invention.

FIG. 4A illustrates the superior portion 55, of coronary artery 58 with a stiffening member 90 disposed therein in accordance with one aspect of the present invention. Aorta 44 communicates with coronary artery 58. In a preferred embodiment, guide catheter 92 is inserted in aorta 44 such that its distal opening 94 is generally aligned with the ostium of coronary artery 58 in aorta 44. Guidewire 96 is then inserted through guide catheter 92, and into coronary artery 58, preferably past the restriction (shown in FIG. 1).

Stiffening member 90 is preferably an apparatus which is suitable for tracking over, or being guided by, guidewire 96.

Stiffening member 90 is preferably formed of a material which is sufficiently rigid to significantly dampen the movement of coronary artery 58 (shown in phantom in FIG. 4A) under the influence of normal heart action. Stiffening member 90 is thus formed of a material sufficiently rigid to stabilize the wall to enable the cardiac thoracic surgeon to safely and efficiently prepare the surgical site for anastomosis, and to ultimately complete the anastomosis associated with the grafting procedure. Stiffening member 90 is preferably coated to minimize trauma to the coronary artery 58. Examples of suitable coatings include, but are not limited to, friction reducing agents such as hydrogel, PTFE, silicon, etc.; soft plastics such as low durometer polymers; and therapeutic agents such as heparin.

Figure 4B:
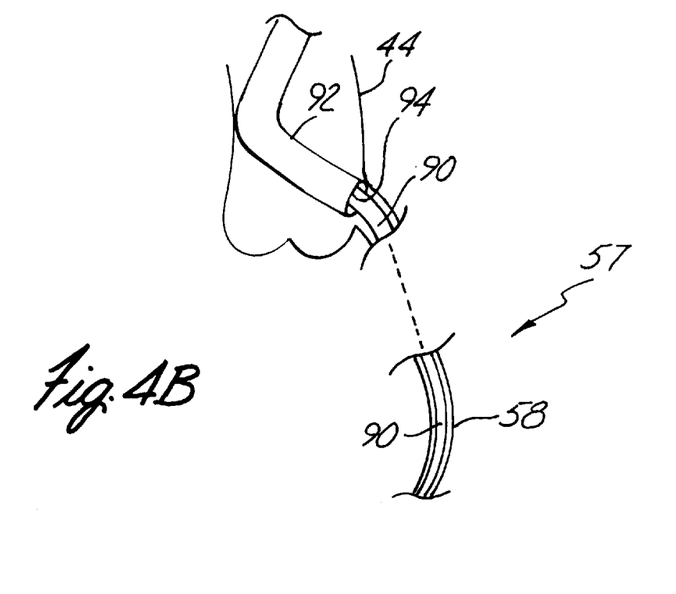
Figure 4C:
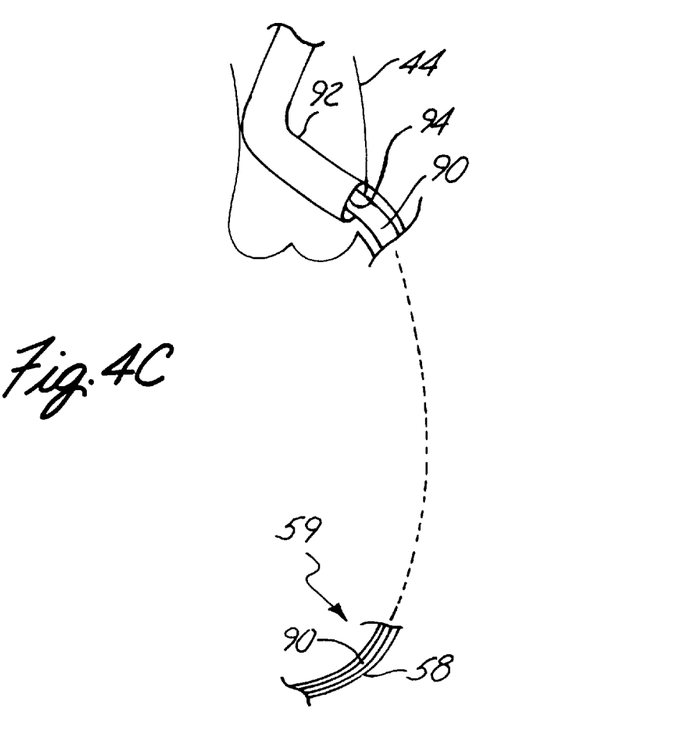

It is contemplated that stiffening member 90 should be designed to adapt to varying curvature of the coronary artery 58. For example, the superior portion 55 of the coronary artery 58 is a relatively gentle curvature corresponding to the shape of the myocardial wall. The marginal portion 57 of the coronary artery 58 as illustrated in FIG. 4B has a relatively tighter radius of curvature. In a similar manner, the inferior portion 59 of the coronary artery 58 as illustrated in FIG. 4C has an even tighter radius of curvature conforming to the myocardial wall. It is desirable that the stiffening member 90 have a geometry and a material composition that enables it to match the curvature of the arterial segments 55, 57 and 59 and the corresponding portion of the heart wall to be stabilized.

Figure 4D:
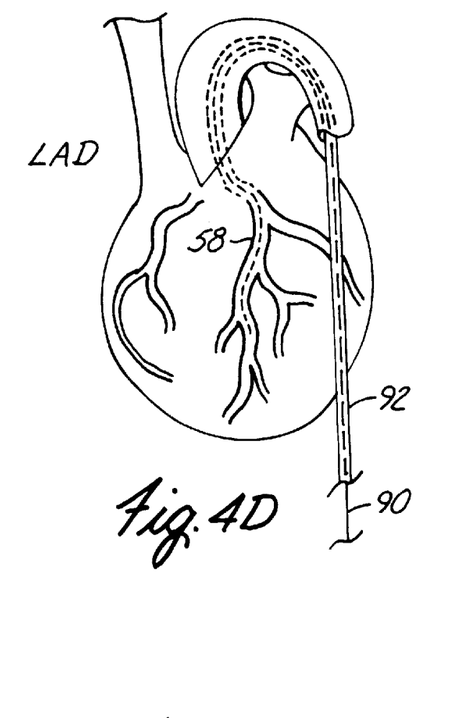
Figure 4E:
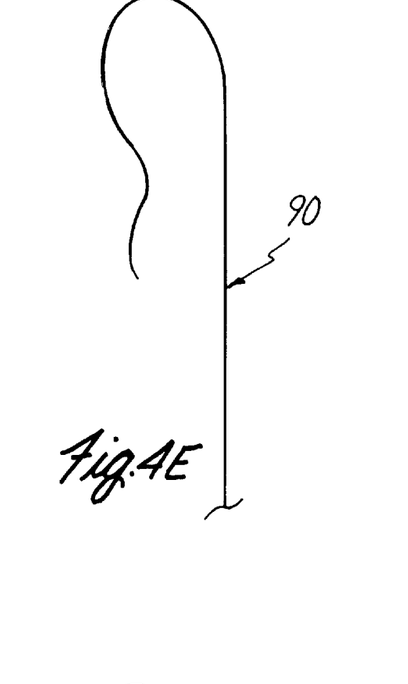
Figure 4F:
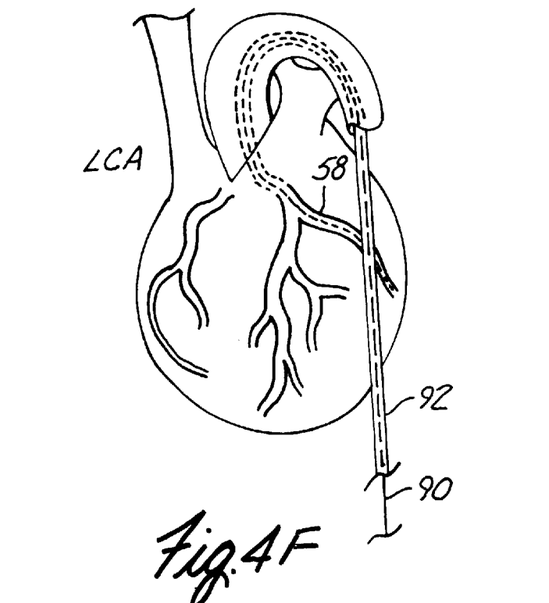
Figure 4G:
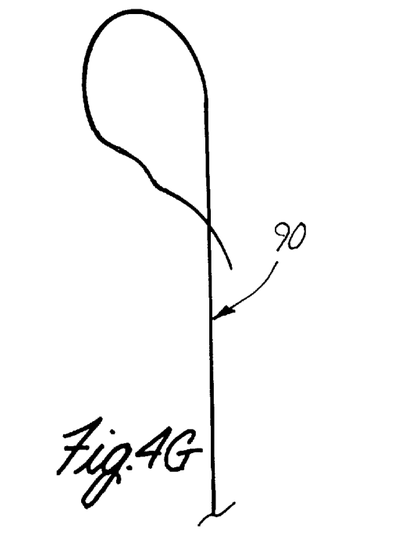
Figure 4H:
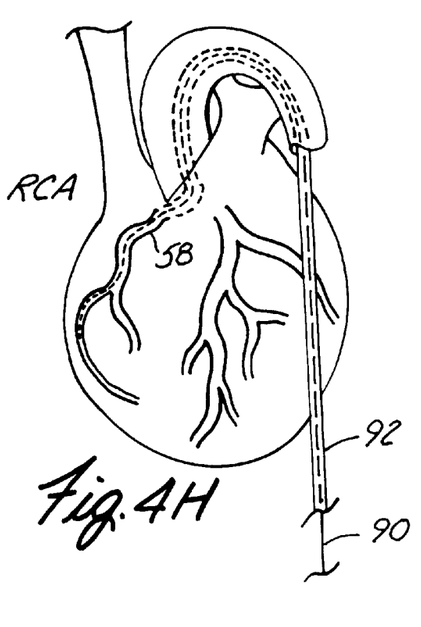
Figure 4I:
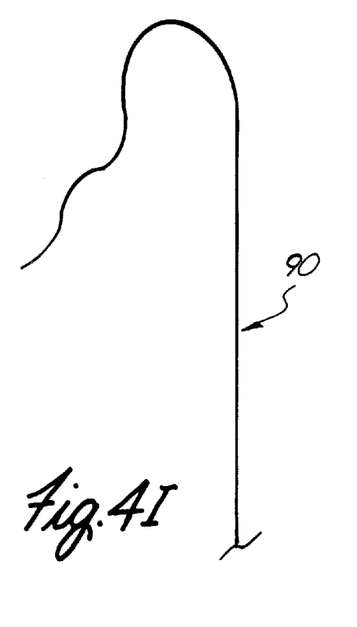

Similarly, it is desirable that the stiffening member 90 be able to adapt to the pattern of the coronary vasculature. With reference to FIGS. 4D and 4E, the left anterior descending (LAD) portion of the coronary artery 58 has a pattern which causes the stiffening member 90 to assume a geometry substantially as depicted in FIG. 4E. With references to FIGS. 4F and 4G, the left circumflex artery (LCA) has a pattern which causes the stiffening member to assume the geometry substantially as depicted in FIG. 4G. In a similar manner, with reference to FIGS. 4H and 4I, the right coronary artery (RCA) has a pattern which causes the stiffening member to assume a geometry substantially as depicted in FIG. 4I. It is apparent from these illustrations that the stiffening member 90 must accommodate a wide variety of geometries having different radii of curvature at different locations along the longitudinal length of the stiffening member 90. Accordingly, it is desirable to have flexible yet pushable portions of the stiffening member 90 at locations in the coronary artery 58 which do not require stabilization. In addition, it is desirable for the stiffening member to be relatively inflexible at locations along the coronary artery 58 where stabilization is desired.

In order to accommodate this need for different regions of flexibility and stiffness along the length of the stiffening member 90, various shaft constructions and materials may be utilized. For example, it may be desirable to use a composite structure in the regions of the stiffening member 90 where stabilization is desired. A suitable composite structure may include a metallic or polymeric braid surrounded by a suitable polymer casing. Alternatively, the outside diameter, inside diameter and wall thickness of the stiffening member 90 may be varied along its length to accommodate regions of flexibility and stiffness. Those skilled in the art will recognize that other constructions may be utilized to accommodate the need for varying regions of flexibility and stiffness.

Figure 5:
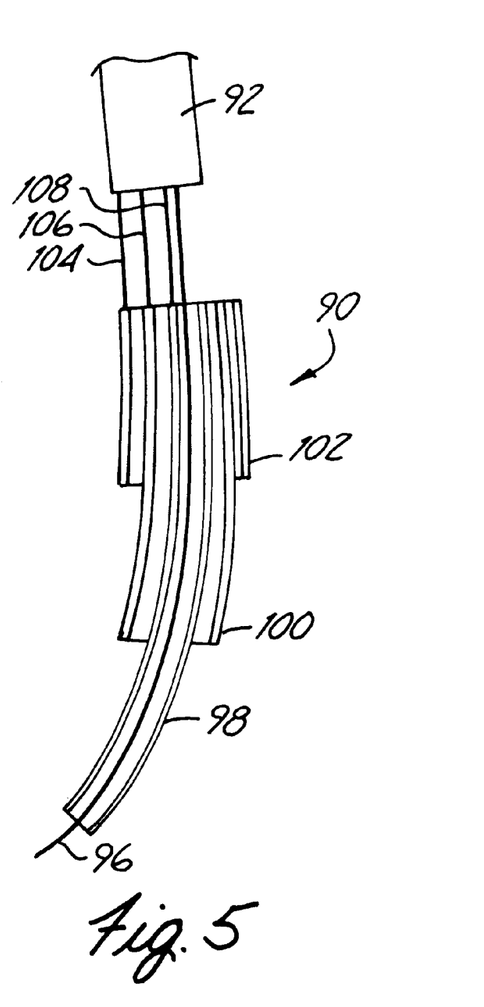
FIG. 5 is a more detailed illustration of a stiffening member in accordance with one aspect of the present invention.

FIG. 5 illustrates one embodiment of the stiffening member 90 in accordance with one aspect of the present invention. Stiffening member 90, shown in FIG. 5, includes a plurality of mandrels or stylets 98, 100, and 102, which are coaxially arranged relative to one another. In one preferred embodiment, stylets 98–102 are formed of stainless steel, Nitinol, or another suitable material. Stylets 98–102 can extend from distal tips thereof to a proximal end of guidewire 96 such that they can be manipulated longitudinally by the physician. However, in another preferred embodiment, stylets 98–102 are generally longitudinally shortened sleeves which are equipped with push wires 104, 106 and 108, which allow the physician to advance stylets 98–102 over wire 96, through guide catheter 92, to the desired stiffening site in coronary artery 58.

A desired number of stylets are advanced over guidewire 96 to the stiffening site until the user observes that movement of the stiffening site has been sufficiently damped. In this way, the user can continue to advance additional stiffening sleeves or mandrels over wire 96 until a desired rigidity or stiffness is achieved. It should also be noted, of course, that each of the mandrels, by themselves, is resilient enough, given its length, to track through the vasculature to the desired stiffening site. However, by coaxially arranging a plurality of the mandrels relative to one another, the rigidity of stiffening member 90 can be increased to a desired extent at the stiffening site.

Figure 6A:
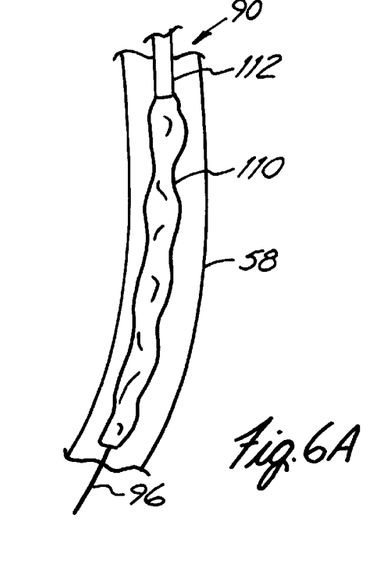
FIGS. 6A–6F illustrate various stiffening members in accordance with another aspect of the present invention.
Figure 6B:
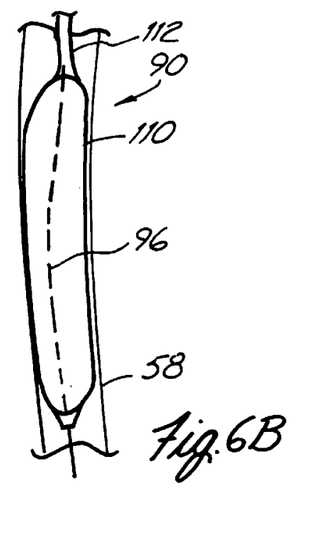

FIGS. 6A and 6B illustrate another embodiment of stiffening member 90, in accordance with one aspect of the present invention. In FIGS. 6A and 6B, stiffening member 90 is a slightly curved balloon 110 supported by a conventional balloon catheter 112. Balloon 110 is preferably formed of a non-pliable balloon material which is preformed to a generally crescent-shape. FIG. 6A illustrates that balloon 110 is preferably first inserted over guidewire 96 into the stiffening site in coronary artery 58 in the deflated position. In the preferred embodiment, prior to inflation, balloon 110 is positioned within artery 58 such that the concave side of balloon 110 (when inflated) faces in a direction generally toward the concave surface of coronary artery 58, at diastole. FIG. 6B illustrates that, once inflated, balloon 110 assumes its preformed generally crescent-shape. When inflated to a sufficient pressure, balloon 110 tends to offset or dampen the motion of coronary artery 58 under the influence of normal heart action.

Figure 6C:
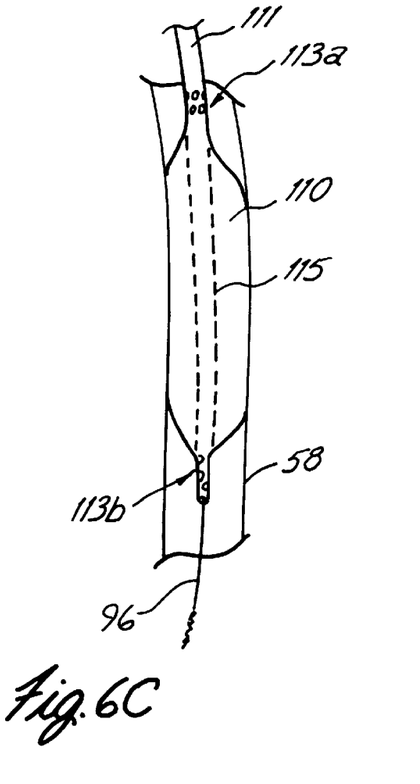

FIG. 6C illustrates another embodiment of the stiffening member 90 in accordance with one aspect of the present invention. In FIG. 6C, the stiffening member is a balloon 110 as described with reference to FIGS. 6A and 6B except that a perfusion catheter 111 is utilized in place of a conventional balloon catheter 112. The perfusion balloon catheter 111 incorporates a series of profusion ports 113A proximal of the balloon and a series of distal perfusion ports 113B distal of the balloon 110. The proximal perfusion portions 113A are in fluid communication with the distal perfusion ports 113B by way of guidewire lumen 115. The guidewire lumen 115 also accommodates the guidewire 96 for advancement and navigation to the desired vascular site. With this arrangement, blood is permitted to pass by the stiffening member 110 when the balloon is inflated for stabilization.

Figure 6D:
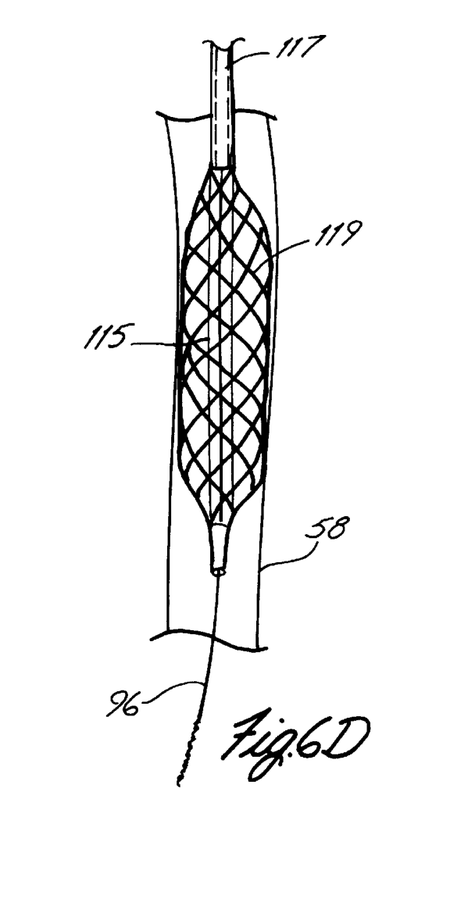

Refer now to FIG. 6D which illustrates another embodiment of the stiffening member 90, in accordance with one aspect of the present invention. In the embodiment illustrated in FIG. 6D, a temporary stent catheter 117 includes an expandable braid structure 119 to stiffen the desired portion of the coronary artery 58. The proximal portion of the braid structure 119 is rigidly connected to the distal end of the shaft of the catheter 117. The distal end of the braid structure 119 is rigidly connected to the guidewire tube 115 which is longitudinally movable with respect to the shaft of the catheter 117. The guidewire 96 is disposed in the guidewire tube 115 as discussed previously. Actuation of the guidewire tube 115 causes the braid structure 119 to collapse or expand. For example, if the guidewire tube 115 is advanced distally with respect to the shaft of the catheter 117, the braid structure 119 will collapse. In a similar manner, if the guidewire tube 115 is pulled proximally relative to the shaft of the catheter 117, the braid structure 119 will expand. In this way, the braid structure 119 may be expanded to stiffen the desired portion of the coronary artery 58.

Figure 6E:
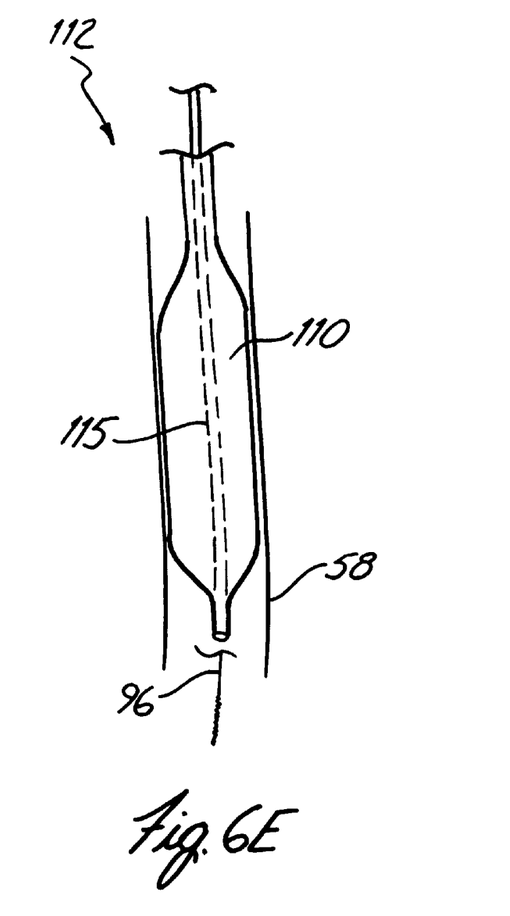
Figure 6F:
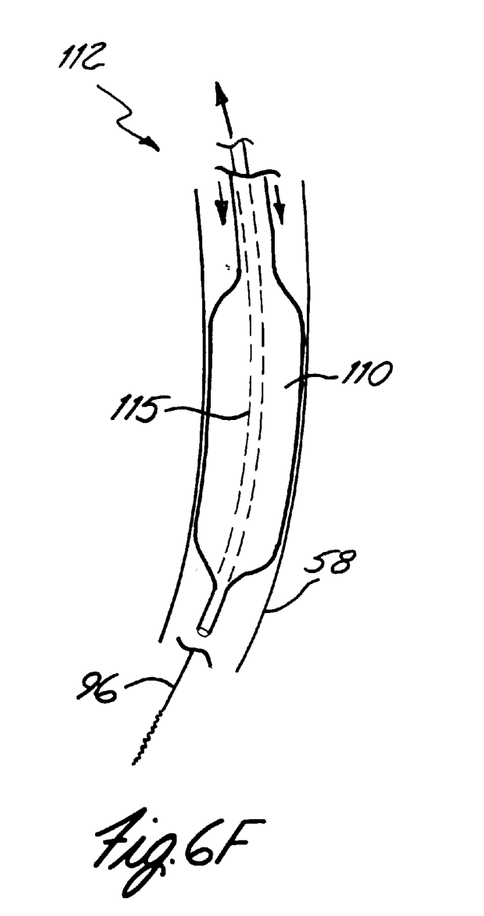

Refer now to FIGS. 6E and 6F which illustrate another embodiment of the stiffening member 90 in accordance with another aspect of the present invention. The balloon catheter 112 illustrated in FIGS. 6E and 6F is similar to the balloon catheter 112 illustrated in FIGS. 6A and 6B except that the shaft of the catheter 112 illustrated in FIGS. 6E and 6F permits longitudinal movement of the guidewire tube 115. Since the proximal end of the inflatable balloon 110 is rigidly connected to the outer portion of the shaft of the catheter 112, and the distal portion of the balloon 110 is rigidly connected to the distal end of the guidewire tube 115, longitudinal actuation of the guidewire tube 115 causes the balloon 110 to assume a crescent shape as illustrated in FIG. 6F. Specifically, when the guidewire tube 115 is pulled proximally relative to the outer tube of the catheter 112, the distal portion of the balloon 110 is pulled in an off-axis direction causing it to assume a crescent shape as illustrated in FIG. 6F. Alternatively, the guidewire tube 115 may be pushed distally relative to the shaft of the catheter 112 such that the balloon 110 is pushed in an off-axis direction causing it to assume a crescent shape. In this way, the treating physician may actuate the guidewire tube 115 causing the balloon 110 to assume a linear shape as illustrated in FIG. 6E or a crescent shape as illustrated in FIG. 6F. It is contemplated that the treating physician could actuate the guidewire tube 115 by hand or utilize a suitable mechanical system to cause the balloon 110 to assume the desired shape in sync with the cardiac cycle. In doing so, the stiffening member 110 would counter the action of the heart wall.

It is further contemplated that the balloon 110 may be pulsated to cycle between relatively flexible and relatively stiff states. In other words, when the balloon 110 is inflated, it assumes a relatively stiff state and when the balloon 110 is deflated, it assumes a relatively flexible state. The balloon 110 may be pulsated in such a manner by utilizing an appropriate inflation device. An example of a suitable inflation device is disclosed in U.S. Pat. No. 5,728,064 to Burns et al. By utilizing a suitable inflation device, the balloon 110 may be pulsated between a non-inflated (i.e., flexible) condition and an inflated (i.e., stiff for stabilization) condition in sync with the cardiac cycle. Synchronization with the cardiac cycle may be accomplished by coupling a suitable mechanical actuator to a conventional ECG apparatus.

Figures 7, 8A, 8B, 9A:
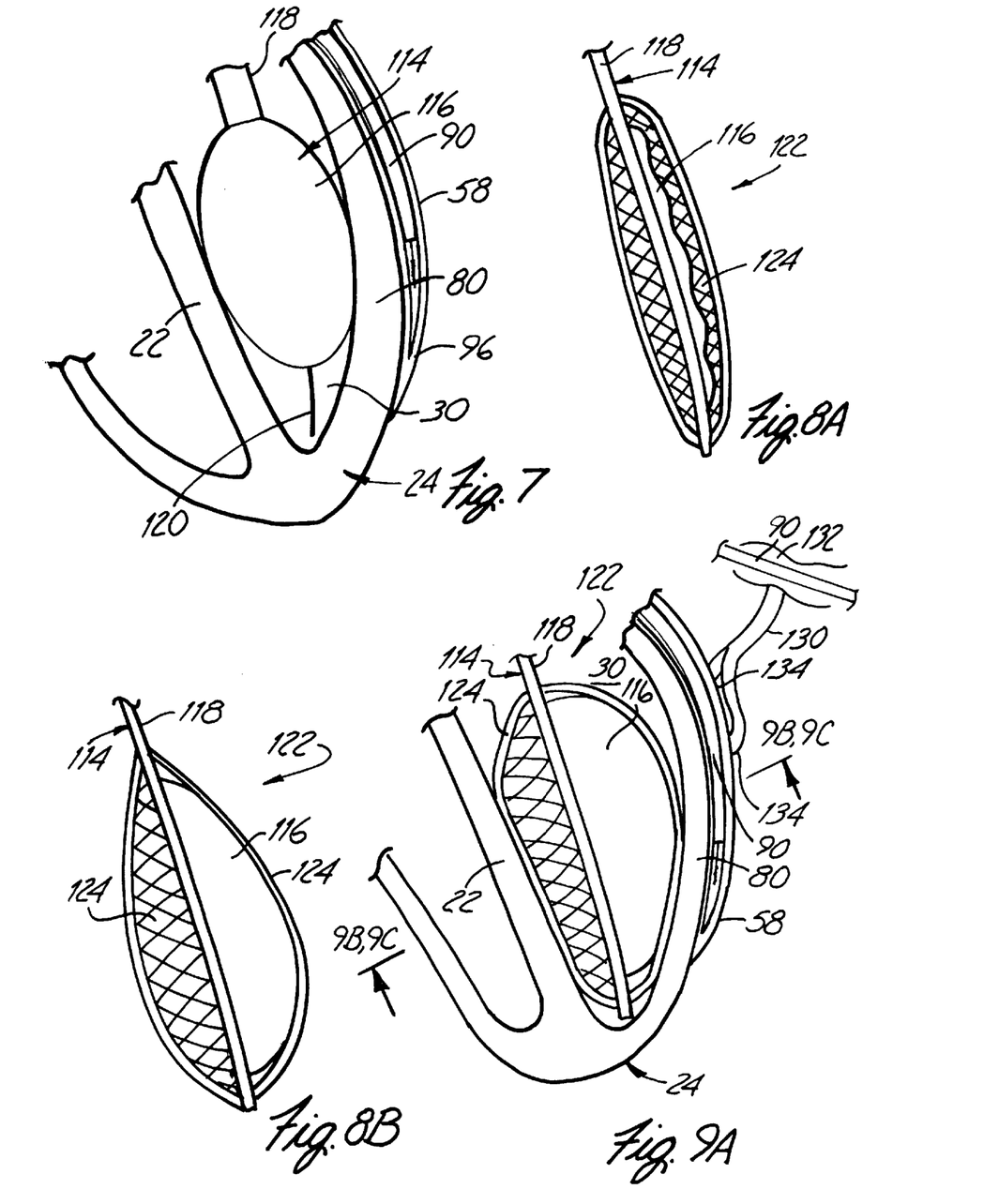
FIG. 7 illustrates the use of a stiffening member in conjunction with a stabilizing member in accordance with one aspect of the present invention.
FIGS. 8A and 8B illustrate another embodiment of a stabilizing member in accordance with another aspect of the present invention.
FIGS. 9A–9C illustrate operation of the stabilizing member shown in FIGS. 8A and 8B.

FIG. 7 illustrates another embodiment of a heart stabilization mechanism in accordance with one aspect of the present invention. FIG. 7 illustrates a greater portion of heart 24 than is illustrated in FIGS. 2A–4. FIG. 7 also illustrates that stiffening member 90 has been inserted to a stiffening site within coronary artery 58. In FIG. 7, a balloon catheter 114 is also inserted into chamber 30 in heart 24. Balloon catheter 114 preferably includes inflatable member, or balloon, 116 and balloon catheter shaft 118.

In one preferred embodiment, the distal portion of balloon catheter 114 is inserted, along a guidewire 120, into chamber 30, through mitral valve 38 in heart 24. Balloon 116 is preferably of sufficient diameter that, when inflated, it not only engages heart wall 80, but it backs up against septum 22. Thus, when inflated, balloon 116 exerts a generally outwardly directed pressure on heart wall 80. Heart wall 80 is thus stabilized between stiffening member 90 and balloon 116, when balloon 116 is in the inflated position.

Of course, it should be noted that stiffening member 90 can be any embodiment of the stiffening member illustrated in previous figures, or any other suitable stiffening member.

In accordance with another aspect of the present invention, balloon 116 can be used to assist in the blood pumping function. Thus, balloon 116 is periodically inflated and deflated, in synchronicity with normal heart contractions, in order to assist in pumping blood from chamber 30.

FIGS. 8A and 8B illustrate another preferred embodiment of a stiffening member 122 which can be disposed in chamber 30, in order to back up stiffening member 90 which is disposed in coronary artery 58. Stiffening member 122 includes balloon catheter 114, with balloon 116 and catheter shaft 118, and also includes a scaffolding or stiffening sleeve 124 disposed about balloon 116. Scaffolding or stiffening sleeve 124 is preferably formed of a wire or a stiff polymer material formed as a mesh, or braid, or of other scaffolding material, which is expandable and retractable with the inflation and deflation of balloon 116. FIG. 8A illustrates stiffening member 122 with balloon 116 in the deflated position, and thus with scaffolding 124 in the collapsed, low profile position.

FIG. 8B illustrates stiffening member 122 with balloon 116 in the inflated position and with scaffolding 124 thus in the expanded position. FIG. 9A illustrates stiffening member 122 in use within chamber 30 of heart 24. Balloon 116 is illustrated in the inflated position. By providing scaffolding 124 over balloon 116, stiffening member 122 provides a substantially stiff surface which supports heart wall 80. This enhances the dampening effect of the stiffening members 90 and 122 on heart wall 80 at the stiffening site.

FIG. 9A also illustrates a bypass graft 130 which extends from a source 132 to a destination 134. Source 132 can be a suitable source for providing bloodflow (as discussed above), while destination 134 is preferably downstream (or distal) of restriction 76 (shown in FIG. 1). It can be seen that stiffening members 90 and 122 provide a stiffening region therebetween which substantially stabilizes heart wall 90 in the area of destination 134. It should also be noted that source vessel 132 can also be provided with a stiffening member 90 in order to stabilize it during anastomosis.

Figure 9B:
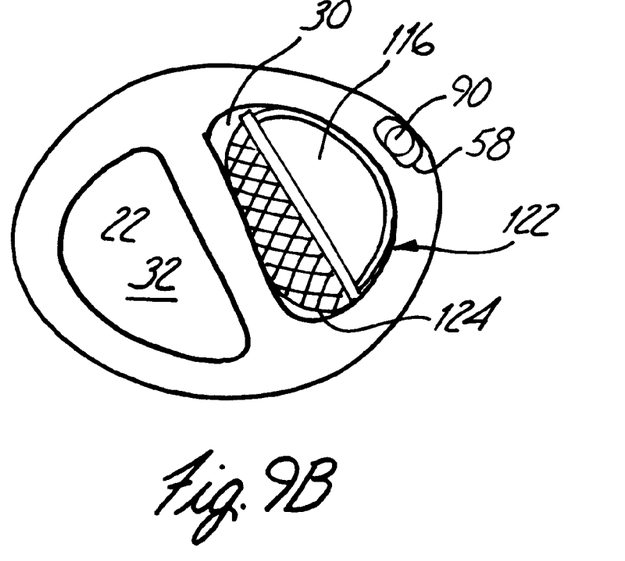
Figure 9C:
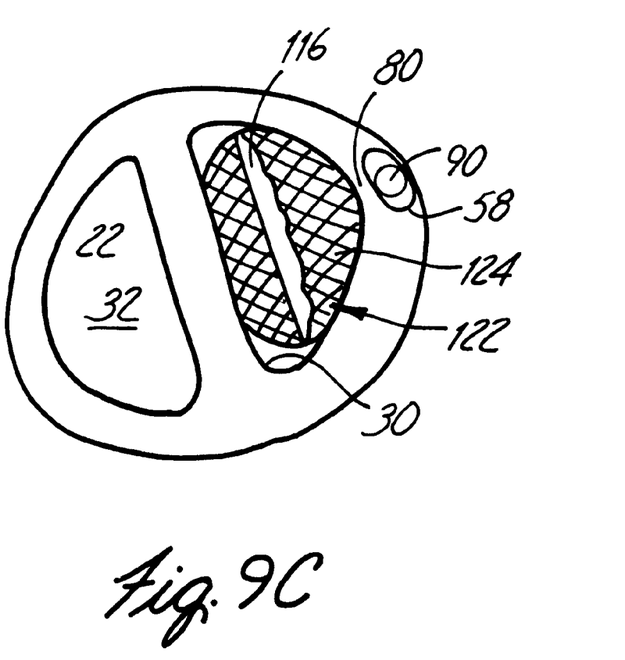

FIGS. 9B and 9C illustrate cross-sections of heart 24 taken along section lines 9B—9B in FIG. 9A. FIG. 9B illustrates a cross-section of heart 24 at diastole, when balloon 116 is inflated. FIG. 9C illustrates heart 24 when balloon 116 is deflated, at systole. In both cases, it can be seen that heart wall 80 is substantially stabilized between stiffening members 90 and 122.

It should also be noted that the present invention can be used in order to stabilize a heart wall, or other vascular tissue, when the heart is stilled with a drug (such as adenozine).

Thus, it can be seen that the present invention provides a transluminal method by which vascular tissue can be stabilized, at a stabilization site, during treatment. A stiffening member can be inserted into a lumen to be treated. Also, a second stiffening member can be inserted inside a chamber of the heart, in order to backup the first stiffening member, stabilizing a portion of the heart wall or vascular tissue between the two stiffening members. This provides a system by which treatment of a vascular restriction, or treatment of other disease, can be accomplished without completely stopping the heart, while providing a substantially static theater of operation to provide easier anastomosis at the stiffening site.

Although the present invention has been described with reference to preferred embodiments, workers skilled in the art will recognize that changes may be made in form and detail without departing from the spirit and scope of the invention.

What is claimed is:

1. A method of treating a restriction in a lumen of a restricted vascular vessel of a mammal, the mammal having a heart contracting to pump blood, comprising:

transluminally deploying a first stabilizing device at a treatment site relative to the restricted vessel to dampen movement of the restricted vessel at the treatment site, caused by contraction of the heart to stabilize the restricted vessel at the treatment site;

transluminally deploying a second treatment device relative to the stabilized treatment site while the first device is deployed and treating the stabilized restricted vessel with the second treatment device; and withdrawing the first stabilizing device and the second treatment device after treatment.

2. The method of claim 1 wherein the first device includes a first stiffening member and comprising:

transluminally advancing the first stiffening member through the lumen of the restricted vessel to the treatment site.

3. The method of claim 2 where the first stiffening member includes a first stiffening sleeve having a lumen therethrough and wherein transluminally advancing the stiffening member comprises:

transluminally advancing a guidewire to the treatment site; and advancing the first stiffening sleeve over the guidewire to the treatment site.

4. The method of claim 3 further comprising:

advancing at least one additional stiffening sleeve over the guidewire to the treatment site.

5. The method of claim 4 wherein advancing the at least one additional stiffening sleeve comprises:

advancing the at least one additional sleeve to the treatment site such that the first stiffening sleeve and the at least one additional stiffening sleeve are in coaxial relation to one another at the treatment site.

6. The method of claim 4 wherein the first stiffening sleeve and the at least one additional stiffening sleeve include associated elongate push rods coupled thereto and wherein the first stiffening sleeve and the at least one additional stiffening sleeve are advanced by:

pushing the associated elongate push rods to advance the first stiffening sleeve and the at least one additional stiffening sleeve to the treatment site.

7. The method of claim 2 wherein the first stiffening member includes a preformed balloon, preformed to a stiffening shape and wherein transluminally advancing the first stiffening member includes:

transluminally advancing the balloon to the treatment site; and inflating the balloon to the stiffening shape.

8. The method of claim 2 wherein the restricted vessel includes a vessel located closely proximate an endocardial wall of the heart, the heart including a chamber defined by an epicardial wall thereof, and further comprising:

transluminally advancing a second stiffening member into the chamber.

9. The method of claim 8 wherein the second stiffening member includes an expandable member and wherein transluminally advancing the second stiffening member includes:

advancing the expandable member into the chamber; and expanding the expandable member such that it contacts the epicardial wall proximate the treatment site in the restricted vessel.

10. The method of claim 9 wherein expanding the expandable member comprises:

expanding and contracting the expandable member based on the contractions of the heart.

11. The method of claim 8 wherein the first and second stiffening members exert generally opposing forces on vascular tissue between the treatment site in the restricted vessel and a contact region of the epicardial wall at which the second stiffening member contacts the epicardial wall.

12. The method of claim 13 wherein the second stiffening member includes an expandable scaffolding and further comprising:

expanding the expandable scaffolding within the chamber such that the contact region is disposed proximate the treatment site.

13. The method of claim 2 wherein treating the stabilized restricted vessel includes providing a conduit between an access site in a source vessel and the restricted vessel and further comprising:

transluminally deploying a second stiffening member through the source vessel to dampen movement of the source vessel at the access site to a desired level.

14. The method of claim 13 wherein one of the restricted vessel and the source vessel is located closely proximate an outer heart wall of the heart having an inner wall defining a chamber, and further comprising:

transluminally deploying a third stiffening member within the heart chamber to exert a stiffening force on the inner wall to dampen movement of the wall of the heart to a desired level.

15. The method of claim 2 wherein the first stiffening member is coated with a material to reduce trauma to the vessel.

16. The method of claim 1 wherein treating the restricted vessel comprises:

coupling a conduit from an access site at a source vessel to the treatment site of the restricted vessel such that the restricted vessel, at the treatment site, is in fluid communication with the source vessel at the access site.

17. The method of claim 16 and further comprising: transluminally stabilizing the source vessel at the access site to dampen movement of the source vessel, caused by contraction of the heart, to a desired level.

18. A kit for stabilizing a treatment site in vascular tissue to be treated, comprising:

a plurality of independent incrementally sized stiffening sleeves, each stiffening sleeve including a proximal and distal end and each stiffening sleeve having an incrementally sized outer diameter and an incrementally sized lumen so that the plurality of stiffening sleeves can be concentrically aligned to form a plurality of radially extending stiffening layers and a plurality of push members coupled to the proximal end of each of the stiffening sleeves to transluminally track the stiffening sleeves to a remote intravascular treatment site while maintaining a portion of plurality of push members external to concentrically align selected stiffening sleeves to form a desired number of stiffening layers to dampen motion at the treatment site, caused by heart contractions, to a desired level.

19. The kit of claim 18 wherein the plurality of stiffening sleeves each comprise a stylet.

20. The kit of claim 18 wherein the plurality of stiffening sleeves are each formed of Nitinol.

21. The kit of claim 18 wherein the plurality of stiffening sleeves are coated with a material to reduce trauma to the vasculature.

22. A kit for dampening movement of a heart comprising:
    a first transluminal device sized for insertion in an intravascular vessel and including a first stiffening member deployable at an intravascular treatment site to dampen movement of a restricted vessel at the treatment site; and
    a second transluminally advanceable device including a second stiffening member formed of an expandable member deployable within a heart chamber to an expanded deployed dimension sized to fill a portion of the heart chamber and circumferentially contact an inner wall of the heart chamber to exert a stabilizing force on the inner wall of the heart chamber proximate the treatment site.

23. The kit of claim 22 wherein the first and second stiffening members are configured to exert generally opposing forces on intervening vascular tissue at the treatment site.

24. The kit of claim 22 wherein the second advanceable device includes:
    an elongate member having a lumen therethrough, a distal end and a proximal end; and
    the expandable member being coupled to the distal end of the elongate member.

25. The kit of claim 24 wherein the expandable member includes:
    an expandable scaffolding sleeve.

26. The kit of claim 25 wherein the expandable member further comprises:
    an inflatable member having an interior in fluid communication with the lumen in the elongate member, the inflatable member being sized such that inflation thereof drives the expandable scaffolding sleeve into an expanded position.

27. The kit of claim 22 wherein the first stiffening member comprises a balloon preformed to a stiffening shape and formed of a non-compliant material movable between a collapsed position and an inflated position and including a catheter having an inflation lumen therethrough in fluid communication with the balloon.

28. A method of stabilizing a desired portion of a heart wall of a heart, comprising:
    transluminally advancing a stiffening member through vasculature into a chamber of the heart; and
    deploying the stiffening member to exert a stiffening force on the desired portion of the heart wall, from within the chamber, to dampen movement of the desired portion of the heart wall to a desired level.

29. The method of claim 28 and further comprising:
    transluminally advancing a second stiffening member into a vessel located closely proximate an outer wall of the heart.

30. The method of claim 29 and further comprising:
    deploying the second stiffening member to exert a force on the heart wall generally opposing the stiffening force exerted by the stiffening member in the chamber of the heart.

31. The method of claim 29 wherein the second stiffening member is coated with a material to reduce trauma to the vessel.

* * * * *